(12) United States Patent
Avellanet

(10) Patent No.: US 6,169,252 B1
(45) Date of Patent: *Jan. 2, 2001

(54) HOLLOW TWISTED AND DRAWN CABLES AND METHOD FOR MAKING THE SAME

(76) Inventor: Francisco J. Avellanet, 1261 Venetia Ave., Coral Gables, FL (US) 33134

( * ) Notice: Under 35 U.S.C. 154(b), the term of this patent shall be extended for 0 days.

This patent is subject to a terminal disclaimer.

(21) Appl. No.: 09/476,195

(22) Filed: Jan. 3, 2000

Related U.S. Application Data

(63) Continuation of application No. 08/963,686, filed on Nov. 4, 1997, now Pat. No. 6,049,042, which is a continuation-in-part of application No. 08/843,405, filed on May 2, 1997, now Pat. No. 5,994,647.

(51) Int. Cl.[7] ..................................................... H01B 5/10
(52) U.S. Cl. ......................................................... 174/128.1
(58) Field of Search ............................. 174/128.1, 128.2, 174/126.1, 125.1

(56) References Cited

U.S. PATENT DOCUMENTS

| | | | |
|---|---|---|---|
| 3,131,469 | 5/1964 | Glaze | 29/470.5 |
| 4,654,477 | 3/1987 | Isoda | 174/128 R |
| 5,448,016 | 9/1995 | DiPaolo et al. | 174/126.1 |
| 5,994,647 | 11/1999 | Avellanet | 174/128.1 |

FOREIGN PATENT DOCUMENTS 197692   5/1923   (GB) .

OTHER PUBLICATIONS

"Trapwire Constructions" in Wire Technology International, by Jerry M. Hesterlee, pp. 51–53, Mar. 1997.

Primary Examiner—Dean A. Reichard
(74) Attorney, Agent, or Firm—David P. Gordon; David S. Jacobson; Thomas A. Gallagher

(57) ABSTRACT

Electrical cables of the present invention include cables made from plated filaments which are first twisted together and then drawn through reducing dies (or swaged). The cables exhibit a conductivity comparable to cables having greater diameter and weight. The smaller diameter of the cables of the invention allows them to be used as leads for electronic components in order to achieve reduced parasitic capacitance without increased resistivity or reactance or component package size. The cold working of the cables of the invention provides them with enhanced flexibility and fatigue strength. The combination of materials used in the cables of the invention provides them with resistance to corrosion and the adverse affects of aging as well as enhanced conductivity. Cables formed according to the invention with a hollow tube core can be self-cooling, or easily cooled by flowing coolant through the hollow core.

24 Claims, 3 Drawing Sheets

HOLLOW TWISTED AND DRAWN CABLES AND METHOD FOR MAKING THE SAME

This application is a continuation of application Ser. No. 08/963,686 filed Nov. 4, 1997, now U.S. Pat. No. 6,049,042, which is a continuation-in-part of application Ser. No. 08/843,405 filed on May 2, 1997, now U.S. Pat. No. 5,994,647, the complete disclosures of which are hereby incorporated by reference herein.

BACKGROUND OF THE INVENTION

1. Field of the Invention

The invention relates to electrical cables. More particularly, the invention relates to electrical cables which exhibit low resistance, high fatigue strength, low weight, good flexibility, cool operation, minimized parasitic capacitance, and which are resistant to the adverse affects of aging and corrosion.

2. State of the Art

My prior application which is referenced above describes the general techniques known in the art for making electrical cables from helically twisted filaments and proposes methods of twisting and drawing wire cables for enhancing the conductivity, flexibility and tensile strength of the cables. In addition to low resistance, flexibility and tensile strength, other characteristics of cables may be important depending on the application in which the cable is used. For example, the ability of a cable to remain cool during operation is often an important consideration. For cables used outdoors for power transmission, resistance to corrosion and low weight of the cable are important considerations. For cables which are subjected to repeated flexion, good flexibility as well as high fatigue strength are important. In cables which are used as leads for semiconductors and other electronic components, parasitic capacitance is an important consideration.

Among the many factors which affect the resistance of an electrical conductor is its temperature. As the temperature of the conductor rises, so does its resistance. Moreover, as the resistance of a conductor is increased, current passing through the conductor will further heat the conductor. Known techniques for cooling electrical conductors are complex and expensive.

The usual method for preventing or minimizing the effects of corrosion on an electrical conductor is to cover it with insulation. However, in many applications such as power transmission cables, insulation can significantly add to the cost of the cable. Most "high tension" power transmission cables are not covered with insulation.

In most cables, their weight is dictated by the choice of materials and the dimensions of the cable. Often, attempts to reduce the weight of the cable results in either increased cost of the materials used to fabricate the cable or an increase in the resistivity of the cable.

Fatigue strength is an important characteristic of electrical conductors which are subjected to flexion such as overhead power cables, flexible power cords, communications cables, and wires used in hand held or portable equipment. The usual method of increasing fatigue strength is to utilize a stranded conductor rather than a solid conductor. As explained in my earlier application, a stranded conductor with the same conductivity of a solid conductor will have a greater cross sectional diameter than the solid conductor. The larger stranded conductor also requires more insulation and has increased parasitic inductance. In addition, as the overall diameter of the insulated stranded conductor increases, so does its stiffness. In general, the stiffness of cylindrical bending beams tends to increase exponentially (to the fourth power) as the diameter is increased. Also, as the number of strands is increased, the ratio of surface area to cross sectional area increases. This makes the cable more vulnerable to the damaging effects of corrosion which significantly decrease the conductivity of the cable as it ages in service.

Parasitic capacitance is a characteristic of electrical conductors which is very important in some applications such as leads for semiconductors and other electrical components. The most common technique for minimizing parasitic capacitance is to make the conductive leads as small as possible and to separate them as much as possible. However, making the leads smaller (in diameter) increases their resistance; and separating the leads from each other results in a larger package size for the component.

As mentioned above, stranded conductors have increased parasitic inductance as compared to solid conductors of the same diameter. This is mostly the result of the individual strands being helically wound rather than being arranged parallel to the axis of the conductor. To the extent that the individual strands are not in perfect electrical contact with each other along their entire length, they tend to behave as individual helical conductors, i.e. as coils. Stranded cables with strands having circular cross section always exhibit imperfect electrical contact among the strands because they contact each other only along a single line. Cables having preformed strands (e.g. "trapezoidal wire") also exhibit imperfect electrical contact among the strands because they contact each other only along portions of their surfaces. An attendant and related problem occurs with customary stranded cables as they age in the presence of air, moisture and other corrosive agents. The buildup of surface corrosion on the strands further reduces the electrical contact among the strands further increasing parasitic inductance.

SUMMARY OF THE INVENTION

It is therefore an object of the invention to provide an electrical cable which has low electrical resistance as well as a method for making the cable.

It is also an object of the invention to provide an electrical cable which has a structure which keeps the cable cool.

It is another object of the invention to provide an electrical cable which has high fatigue strength, low weight and good flexibility.

It is still another object of the invention to provide an electrical cable which is resistant to the adverse affects of aging and corrosion.

Yet another object of the invention is to provide an electrical cable which exhibits reduced parasitic capacitance and inductance.

In accord with these objects which will be discussed in detail below, the electrical cables of the present invention include cables made from plated filaments which are first twisted together and then drawn through reducing dies (or swaged), filaments which are twisted together around a core material which melts or otherwise deforms during drawing of the cable through reducing dies (or swaging of the cable), filaments which are twisted around a tube prior to drawing through reducing dies (or swaging), and cables which are made from combinations of these methods. Presently preferred plating materials include silver and gold. Presently preferred core materials include silver and solder. A presently preferred core tube is a steel tube.

The cables of the invention exhibit a conductivity comparable to cables having greater diameter and weight. The smaller diameter of the cables of the invention allows them to be used as leads for electronic components in order to achieve reduced parasitic capacitance without increased resistivity or component package size. The cold working of the cables of the invention provides them with enhanced flexibility and fatigue strength. The combination of materials used in the cables of the invention provides them with resistance to corrosion and the adverse affects of aging as well as enhanced conductivity. Cables formed according to the invention with a hollow tube core can be cooled by flowing a coolant through the hollow core. In addition, the hollow core provides improved heat rejection properties because no heat is generated in the core where current does not flow. The hollow tube core also enhances fatigue strength, resists the effects of aging, and lowers the weight of the cable. Cables formed with a silver core, as opposed to a hollow core, are also self-cooling by means of having a lower resistance thermal path from the core of the cable to its surface.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
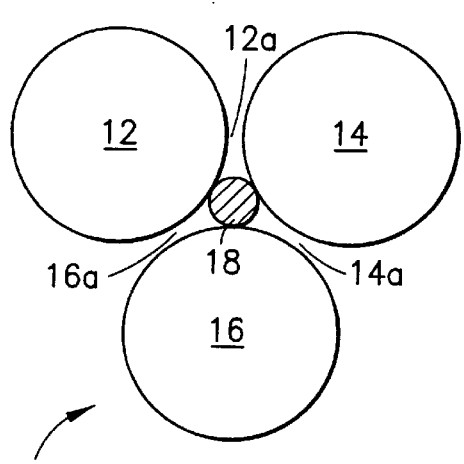
FIG. 1 is a cross sectional view of a cable assembly according to a first embodiment of the invention prior to drawing through reducing dies.
Figure 3:
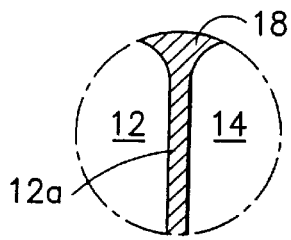
FIG. 3 is an enlarged view of the portion labelled A in FIGS. 2 and 5.
Figure 2:
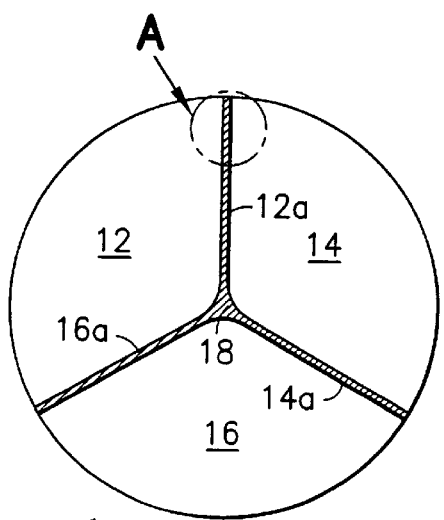
FIG. 2 is a cross sectional view of a finished cable assembly according to a first embodiment of the invention.

Referring now to FIGS. 1 through 3, a first embodiment of a cable 10 according to the invention includes three copper (or aluminum) strands 12, 14, 16 which are twisted around a central strand 18 which is preferably made of silver, gold or solder. The bundle of twisted strands is then drawn, as described in the previously incorporated parent application, through at least one reducing die such that the overall diameter of the twisted assembly is reduced by at least approximately 9%, preferably through at least two dies such that the overall diameter is reduced by at least approximately 18%, and more preferably through a plurality of reducing dies such that the overall diameter of the twisted assembly is reduced, preferably by at least 30–40%. Alternatively, the bundle may be swaged to reduce its diameter. The drawing (or swaging) process causes the inner core 18 to flow into the interspaces 12a, 14a, 16a between the copper (or aluminum) strands 12, 14, 16 as shown best in FIGS. 2 and 3. The resultant cable 10 possesses lower resistance than a cable of the same diameter made of three twisted copper (or aluminum) strands. The central silver core 18 enhances the electrical connection of the three strands 12, 14, 16 and also provides a self-cooling center of the cable. Since the thermal conductivity of silver is greater than that of copper (or aluminum), its electrical conductivity is higher than that of copper (or aluminum) at the same temperature. The overall resistivity of silver is lower than that of copper (or aluminum). Thus, as the cable 10 warms from the center, its conductivity remains higher than a similar cable without a silver core (or without a core of higher conductivity). If the central core 18 is made of gold, it will also possess an inherently higher conductivity and the cable will be less affected by heat than a similar cable without the core because an improved thermal path exists to conduct heat from the core to the surface of the conductor. It will also be appreciated that when solder is used as the core, the cable may be more easily soldered to an electrical connection or to another cable.

The above-described cable having a conductive filler material among the strands will have increased conductivity and reduced parasitic inductance as compared to a stranded cable of similar size with no filler material. Increased conductivity will result from the intimate electrical connection established among the strands by the conductive filler material. This connection will allow current to flow more freely along the longitudinal axis of the cable rather than along longer and higher resistance paths of individual helical strands. In addition, by allowing the current to flow parallel to the longitudinal axis, parasitic inductance is significantly decreased. It will be appreciated that when the cable is used to carry an alternating current, the cable will exhibit reduced inductive reactance for these same reasons.

Figure 4:
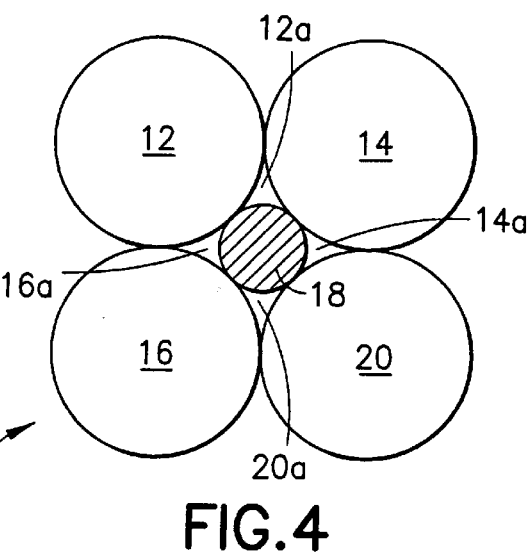
FIG. 4 is a cross sectional view of a cable assembly according to a second embodiment of the invention prior to drawing through reducing dies.
Figure 5:
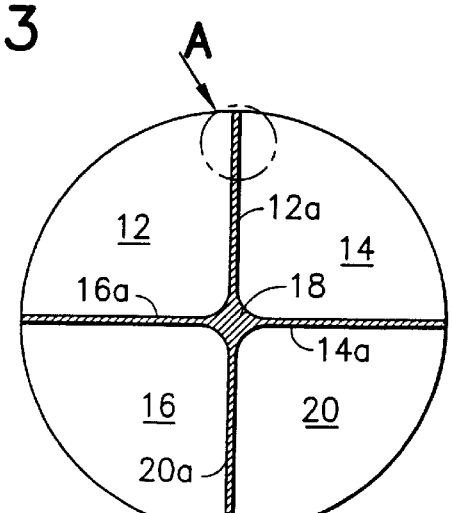
FIG. 5 is a cross sectional view of a finished cable assembly according to a second embodiment of the invention.

The methods described above may be applied to a cable having more than three strands. For example, as shown in FIGS. 4 and 5, according to a second embodiment of the invention, four copper (or aluminum) strands 12, 14, 16, and 20 are twisted around a central core 18 which is preferably made of silver, gold or solder. The twisted strands are then drawn through a plurality of reducing dies as described in the previously incorporated parent application such that the overall diameter of the twisted assembly is reduced, preferably by at least approximately 18%, and more preferably by at least 30–40%. The drawing (or swaging) process causes the inner core 18 to flow into the interspaces 12a, 14a, 16a, 20a between the copper (or aluminum) strands 12, 14, 16, 20 as shown best in FIGS. 3 and 5. The resultant cable 30 has similar properties as the cable 10 described above. Those skilled in the art will appreciate that more than four copper (or aluminum) strands may also be twisted around a central core and drawn or swaged as described above.

Figure 6:
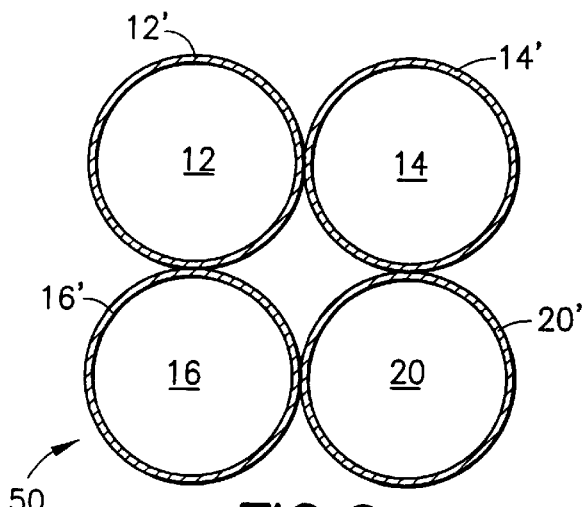
FIG. 6 is a cross sectional view of a cable assembly according to a third embodiment of the invention prior to drawing through reducing dies.
Figure 7:
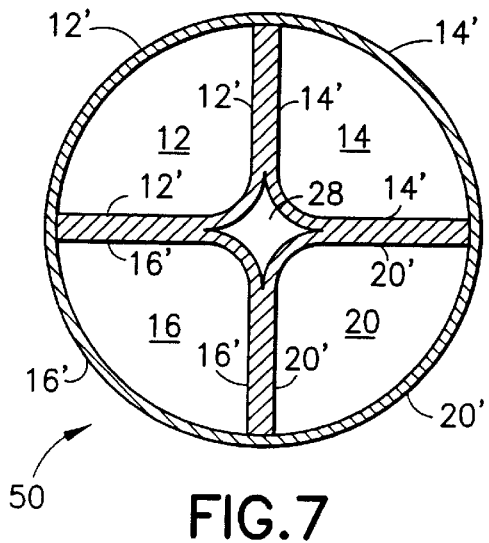
FIG. 7 is a cross sectional view of a finished cable assembly according to a third embodiment of the invention.

Turning now to FIGS. 6 and 7, a cable 50 according to a third embodiment of the invention is made from four copper (or aluminum) strands 12, 14, 16, 20 which are each plated with an outer coating 12', 14', 16', 20' of gold or silver. The strands are twisted and the twisted strands are drawn through a plurality of reducing dies as described in the previously incorporated parent application such that the overall diameter of the twisted assembly is reduced, preferably by at least approximately 18%, and more preferably by at least 30–40%. The drawing (or swaging) process causes the plating 12', 14', 16', 20' to flow together as shown in FIG. 7. As shown in FIG. 7, a hollow core 28 remains at the center of the cable after the twisted strands are drawn or swaged. This may be advantageous to keep the cable cool as discussed above. However, the cable 50 may be drawn with a central core like the cables 10 and 30 described above to maximize conductive cross sectional area.

The cable 50 according to the invention provides several other interesting advantages. For example, given that the plating material covering the strands is more resistant to corrosion than the copper or aluminum strands, the cable 50 will exhibit superior resistance to corrosion and the effects of aging. As explained above, this will prevent the cable from developing increased resistance over time and will forestall increases in parasitic inductance. Thus, plating the strands with silver, palladium, or gold and drawing or swaging as described above provides increased conductivity as well as a significantly longer useful life for the cable. It is believed that the advantages gained in conductivity and longer useful life are economically significant relative to the increased cost of plating the strands. For example, plating or otherwise coating strands with a thin (approx. 0.1 to 10 microns) layer of gold or palladium should prevent corrosion. Plating or otherwise coating strands with a layer of silver (approx. 10 to 500 microns) will result in a cable which, when exposed to common corrosive agents, will develop a conductive silver oxide or conductive silver salt on its surface. While the silver coating does not prevent corrosion, it prevents the adverse effects of corrosion on the electrical properties of the cable. Coating the strands with layers of this thickness and of these materials will not add significantly to the cost of manufacture compared to the value in improved performance for the cable.

From the foregoing, those skilled in the art will appreciate that the combined process of plating, twisting, and drawing or swaging provides an unexpected combination of advantages which include: enhanced conductivity, increased useful life, prevention against the effects of corrosion, and reduced parasitic inductance. Moreover, it will be appreciated that the combined advantages are greater than what would be expected from combining the individual effects of plating, twisting, and drawing.

Figure 8:
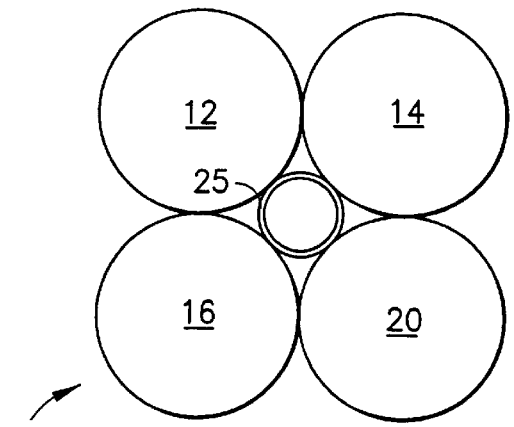
FIG. 8 is a cross sectional view of a cable assembly according to a fourth embodiment of the invention prior to drawing through reducing dies.
Figure 9:
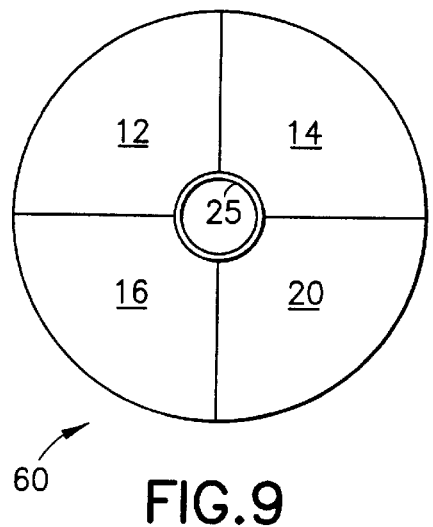
FIG. 9 is a cross sectional view of a finished cable assembly according to a fourth embodiment of the invention.

FIGS. 8 and 9 illustrate a cable 60 according to a fourth embodiment of the invention. Four copper (or aluminum) strands 12, 14, 16, 20 are twisted around a hollow tube 25 which is preferably made of stainless steel. The assembled strands and tube are drawn through a plurality of reducing dies as described in the previously incorporated parent application such that the overall diameter of the twisted assembly is reduced, preferably by at least approximately 18%, and more preferably by at least 30–40%. The resulting cable 60 is provided with a hollow core formed by the tube 25. According to an alternate embodiment of the invention, the tube 25 may be filled with a coolant, or a coolant may be pumped through the tube 25.

Figure 10:
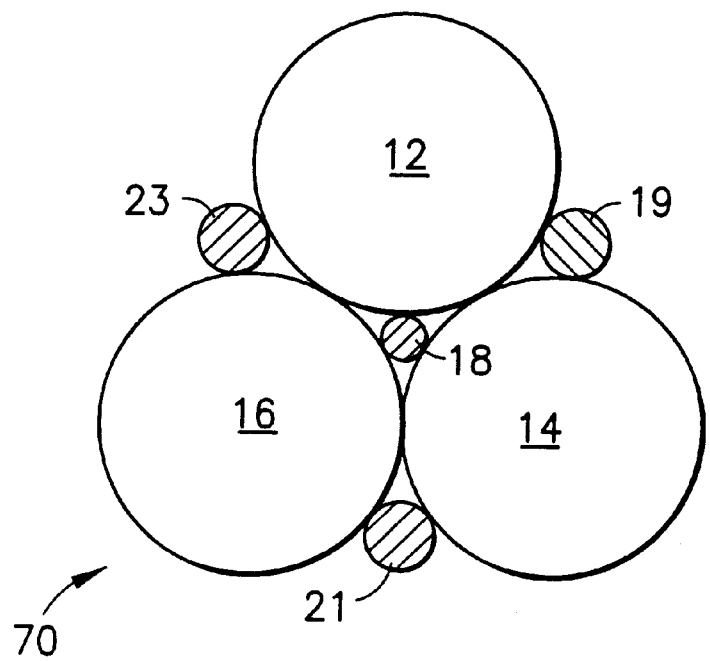
FIG. 10 is a cross sectional view of a cable assembly according to a fifth embodiment of the invention prior to drawing through reducing dies.
Figure 11:
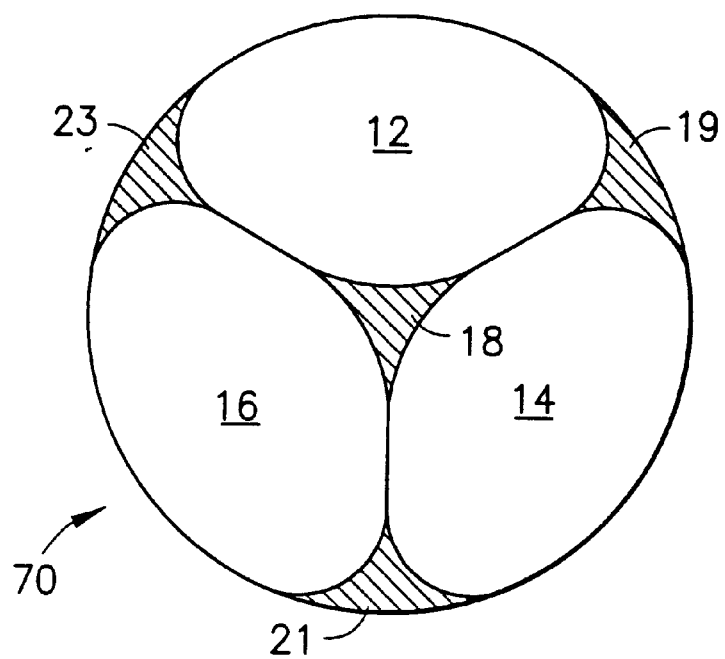
FIG. 11 is a cross sectional view of a finished cable assembly according to a fifth embodiment of the invention.

Turning now to FIGS. 10 and 11, a cable 70, according to a fifth embodiment of the invention, includes three copper (or aluminum) strands 12, 14, 16, which may be plated as described above, and four silver strands 18, 19, 21, 23. The three copper (or aluminum) strands 12, 14, 16 are twisted around one of the silver strands 18, and the other three silver strands 19, 21, 23 are laid in the spaces between the copper (or aluminum) strands and twisted as shown in FIG. 10. The bundle of strands is drawn through a plurality of reducing dies as described in the previously incorporated parent application such that the overall diameter of the twisted assembly is reduced, preferably by 30–40%. The drawing (or swaging) process causes the silver to flow into and fill the spaces between the copper (or aluminum) strands as shown in FIG. 11.

As mentioned above, the fatigue strength of electrical cables is an important factor for cables subjected to repeated flexion. The present invention, as demonstrated in the foregoing exemplary embodiments, provides a higher fatigue strength than conventional stranded cables for three reasons. First, the reduced overall diameter and more compact form of a cable according to the invention will have a smaller cross sectional area as compared to a stranded cable having similar conductivity. Thus, the cable according to the invention will have a smaller section polar moment which will result in lower stress and strain on the strands when the cable is bent around a given radius. The reduction in stress and strain results in a higher fatigue life. Second, by increasing the degree of twist in a stranded cable, the flexibility of the cable can be increased. Normally this is not recommended since increasing the twist angle adversely affects conductivity and increases parasitic inductance, especially after aging. With the present invention, however, the adverse effects of a high twist angle are mitigated by drawing or swaging. Therefore, the increased flexibility of a high twist angle can be achieved without the adverse effects. Third, the effects of cold working during drawing or swaging of copper and aluminum conductors causes an increase in yield strength in these materials, which also improves the fatigue life of the cable. Fourth, drawing strands of wires through dies produces a highly polished surface, as the surface is burnished during the drawing process. Such a surface facilitates the extrusion of an insulative coating over the cable.

While all of the exemplary embodiments given herein refer to ohmic conductors such as copper, aluminum, cold, and silver, it should be understood that the advantages of the invention also apply to cables where the strands or the plating on the strands or the conductive filler are made of superconductive material, including low-temperature superconductors such as niobium—titanium, or high-temperature superconductors such as copper-based ceramic formulations known in the art.

There have been described and illustrated herein several embodiments of electrical cables and methods of making electrical cables. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as so claimed.

What is claimed is:

1. A cable, comprising:
   a plurality of strands twisted to form a bundle in which no one of said plurality of strands forms a center core strand of said bundle, said bundle drawn through at least one die or swaged to form a cable having a hollow center after being drawn.

2. A cable according to claim 1, wherein:
   said plurality of strands is exactly four strands.

3. A cable according to claim 1, wherein:
said cable has a diameter reduced by at least 9% relative to said bundle.

4. A cable according to claim 1, wherein:
said cable has a diameter reduced by at least 18% relative to said bundle.

5. A cable according to claim 1, wherein:
said cable has a diameter reduced by at least 30% relative to said bundle.

6. A cable according to claim 1, wherein:
at least one of said strands includes a base first material and is plated with a second material different than said first material.

7. A cable according to claim 6, wherein:
said second material is softer than said first material.

8. A cable according to claim 6, wherein:
said second material is more conductive than said first material.

9. A cable according to claim 6, wherein:
said first material is one of copper and aluminum.

10. A cable according to claim 6, wherein:
said second material is one of silver, gold, and palladium.

11. A cable, comprising:
a plurality of strands each having a same non-circular transverse cross-sectional shape such that together said plurality of strands form a cable having a substantially circular cross-section and an interior longitudinal hollow portion through a longitudinal axis of said cable.

12. A cable according to claim 11, wherein:
at least one of said strands includes a base first material and is plated with a second material different than said first material.

13. A cable according to claim 12, wherein:
said second material is softer than said first material.

14. 36. A cable according to claim 12, wherein:
said second material is more conductive than said first material.

15. A cable according to claim 12, wherein:
said first material is one of copper and aluminum.

16. A cable according to claim 12, wherein:
said second material is one of silver, gold, and palladium.

17. A method of making an electrical cable, comprising:

a) twisting a plurality of strands to form a bundle in which no one strand is a central core strand, wherein at least one of said strands includes a base first material and is plated with a second material different than said first material; and b) compacting said bundle by drawing through at least one die or swaging to form a conductive cable having a substantially circular transverse cross section and a longitudinal hollow portion through a longitudinal axis of said cable.

18. A method according to claim 17, wherein:
said second material is softer than said first material.

19. A method according to claim 17, wherein:
said second material is more conductive than said first material.

20. A method according to claim 17, wherein:
said first material is one of copper and aluminum.

21. A method according to claim 17, wherein:
said second material is one of silver, gold, palladium.

22. A method according to claim 17, wherein:
said cable has a diameter reduced by at least 9% relative to said bundle.

23. A method according to claim 17, wherein:
said cable has a diameter reduced by at least 18% relative to said bundle.

24. A method according to claim 17, wherein:
said cable has a diameter reduced by at least 30% relative to said bundle.

* * * * *